United States Patent [19]

Gornowicz et al.

[11] Patent Number: 5,660,690

[45] Date of Patent: Aug. 26, 1997

[54] METHOD FOR DISTILLING HEXAMETHYLCYCLOTRISILOXANE

[75] Inventors: Gerald Alphonse Gornowicz; Rocco Joseph Voci, both of Midland, Mich.

[73] Assignee: Dow Corning Corporation, Midland, Mich.

[21] Appl. No.: 657,210

[22] Filed: Jun. 3, 1996

[51] Int. Cl.$^6$ .................... B01D 3/34; C07F 7/20
[52] U.S. Cl. .................... 203/1; 203/6; 203/68; 203/69; 203/70; 556/460
[58] Field of Search .................... 203/68–69, 6, 203/70, 1, 91; 528/14; 556/456, 430, 453, 460

[56] References Cited

U.S. PATENT DOCUMENTS

| | | | |
|---|---|---|---|
| 4,774,346 | 9/1988 | Imai | 556/456 |
| 5,233,068 | 8/1993 | Fukushima et al. | 556/430 |
| 5,399,649 | 3/1995 | Okawa | 528/14 |

FOREIGN PATENT DOCUMENTS

| | | |
|---|---|---|
| 0223513 | 5/1987 | European Pat. Off. . |
| 664492 | 7/1995 | European Pat. Off. . |

*Primary Examiner*—Virginia Manoharan
*Attorney, Agent, or Firm*—Alexander Weitz

[57] ABSTRACT

The invention relates to an improved distillation method wherein hexamethylcyclotrisiloxane is isolated from a crude blend thereof by mixing the crude blend with a hydrocarbon co-solvent having a normal boiling point of 125° C. to 150° C. and distilling the resulting mixture in an apparatus having a reboiler, a fractionating column and a condenser, whereby deposition of solid hexamethylcyclotrisiloxane in the condenser is eliminated.

22 Claims, No Drawings

METHOD FOR DISTILLING HEXAMETHYLCYCLOTRISILOXANE

FIELD OF THE INVENTION

The present invention relates to a method for distilling hexamethylcyclotrisiloxane. More particularly, the invention relates to an improved method for distilling hexamethylcyclotrisiloxane from a crude blend thereof, the improvement comprising adding a hydrocarbon co-solvent to the crude blend prior to distillation, whereby deposition of solid hexamethylcyclotrisiloxane in the condenser section of the distillation apparatus is greatly reduced or entirely eliminated.

BACKGROUND OF THE INVENTION

Hexamethylcyclotrisiloxane, otherwise known as cyclic trimer or $D_3$ in the silicone art, can be anionically polymerized, and subsequently capped with a functional silane, to prepare a so-called "macromonomer" having a very narrow molecular weight distribution (see, for example, U.S. Pat. No. 5,399,649 to Okawa and European Patent Publication No. 0 664 492 A2 to Shin-Etsu Chemical Co.). These macromonomers, in turn, find utility in the synthesis of graft or block interpolymers with various organic systems. However, in order to be effective as a starting material, the hexamethylcyclotrisiloxane must separated from octamethylcyclotetrasiloxane and other impurities generally found in the crude feeds containing this product.

In commercial production, a crude mixture containing hexamethylcyclotrisiloxane may be recovered, e.g., as a byproduct from the hydrolysis of dimethyldichlorosilane, typically in the presence of an organic solvent. Although the primary object of this process is the formation of hydroxy-terminated polydimethylsiloxane and octamethylcyclotetrasiloxane, significant quantities of hexamethylcyclotrisiloxane and, to a lesser extent, cyclopolysiloxanes having greater degrees of polymerization, are also formed under the highly acidic hydrolysis conditions. The crude mixture of volatiles obtained from the hydrolysis process must then be distilled to separate the hexamethylcyclotrisiloxane from the octamethylcyclotetrasiloxane, higher cyclopolysiloxanes and other impurities. Likewise, when the crude blend is obtained from a base-catalyzed equilibration of a polydimethylsiloxane or mixture of polydimethylsiloxanes, it must also be distilled to separate the hexamethylcyclotrisiloxane from the higher cyclopolysiloxanes and other impurities.

When such an operation is attempted using conventional fractional distillation equipment comprising a reboiler, column and condenser, solid hexamethylcyclotrisiloxane (melting point=64° C.) starts to deposit in the condenser and eventually blocks or severely restricts overhead throughput. Of course, changes in condenser design can be implemented to overcome this difficulty. Likewise, the distillation can be carried out at an elevated pressure (and condenser temperature) to minimize this effect. But both of these remedies require additional capital outlay and are not generally compatible with existing equipment constraints.

There is therefore a need for a method which will allow the isolation of hexamethylcyclotrisiloxane which is suitable for use in the synthesis of macromonomers from the above described crude blend using conventional distillation equipment.

SUMMARY OF THE INVENTION

A distillation method has now been discovered wherein hexamethylcyclotrisiloxane is isolated from other volatile byproducts and impurities of the above described crude blend obtained from the hydrolysis of dimethyldichlorosilane. Moreover, the instant method does not require special reaction conditions or modifications to conventional distillation equipment and the hexamethylcyclotrisiloxane solution obtained may be used directly in the above mentioned macromonomer synthesis.

The present invention, therefore, relates to a method for distilling hexamethylcyclotrisiloxane from a crude blend thereof, said method comprising (I) mixing said crude blend with a hydrocarbon co-solvent having a normal boiling point of 125° C. to 150° C.; and (II) distilling the mixture formed in step (I) in an apparatus comprising a reboiler, a fractionating column and a condenser.

DETAILED DESCRIPTION OF THE INVENTION

As stated above, the undesired deposition of solid hexamethylcyclotrisiloxane in the condenser of a conventional distillation apparatus is essentially prevented by the method of the present invention when a crude blend (A) of the hexamethylcyclotrisiloxane is fractionally distilled in the presence of the hydrocarbon co-solvent (B).

In a preferred embodiment, the crude blend (A) is a volatile byproduct obtained from the above described hydrolysis of dimethyldichlorosilane. In addition to hexamethylcyclotrisiloxane and low boiling organic solvent used to facilitate the hydrolysis (e.g., hexane, heptane), this crude blend (A) contains octamethylcyclotetrasiloxane and cyclopolysiloxane having degrees of polymerization (DP) of 5. It also typically contains trace amounts of silanol-functional siloxanes, hydrochloric acid and low boiling chlorinated hydrocarbon compounds.

According the method of the present invention, the above described crude blend (A) is mixed with a hydrocarbon co-solvent (B) having a normal boiling point (i.e., b.p. at 1 atmosphere) of about 125° C. to about 150° C., preferably 130° C. to 140° C. The resulting mixture is then distilled in an apparatus comprising a reboiler, a fractionating column and a condenser (i.e., a conventional fractional distillation unit).

When the distillation is carried out in batch fashion, the first overhead fraction contains the low boiling organic solvent from the hydrolysis reaction as well as the hydrochloric acid and most of the trace impurities described supra. Since the boiling points of the hexamethylcyclotrisiloxane (normal b.p.=about 134° C.) and the hydrocarbon co-solvent (B) are close to one another, the second overhead fraction consists essentially of a mixture of these two components. Octamethylcyclotetrasiloxane and higher cyclopolysiloxanes concentrate in the reboiler (pot).

The above distillation can also be accomplished as a continuous operation. In this case, two distillation units are preferably employed. Crude blend (A) is fed to the column of the first distillation unit and the organic solvent, hydrochloric acid and the majority of the other impurities, described supra, are taken off in an overhead stream through a first condenser. The high boiler stream from a first reboiler is fed to the column of the second distillation unit, along with a stream of co-solvent (B). The overhead stream from the second unit passes through a second condenser and consists essentially of a mixture of hexamethylcyclotrisiloxane and co-solvent (B). The bottom stream from the second unit is a mixture of octamethylcyclotetrasiloxane and the higher cyclopolysiloxanes, as in the case of batch distillation.

For the purposes of the present invention, the amount of co-solvent (B) is preferably adjusted such that the concentration of the hexamethylcyclotrisiloxane in the hexamethylcyclotrisiloxane/co-solvent overhead fraction (or overhead stream) is about 30 to about 50 weight percent, preferably about 40%. When this concentration is less than about 30 weight %, the method becomes inefficient with respect energy consumption since more co-solvent than necessary to prevent deposition of solid hexamethylcyclotrisiloxane in the condenser is present in the overhead. Moreover, a mixture having such a low concentration of hexamethylcyclotrisiloxane is not conducive to the above described synthesis of macromonomer. On the other hand, when the distillation is carried out at ordinary atmospheric pressure and the level of hexamethylcyclotrisiloxane in the overhead is greater than about 50 weight %, deposition of solid hexamethylcyclotrisiloxane is observed in the condenser (e.g., the second condenser in the case of continuous distillation).

For the purposes of the invention, co-solvent (B) must be inert with respect to reaction with any component of the crude blend (A). Further, as stated above, the hydrocarbon co-solvent (B) must have a normal boiling point of about 125° C. to about 150° C. When the normal boiling point is less than about 125° C. (e.g., toluene; normal b.p.=111° C.) the co-solvent distills as a separate fraction and deposition of solid hexamethylcyclotrisiloxane is observed in the condenser as the distillation is continued. Likewise, when the normal boiling point is greater than about 150° C., the co-solvent concentrates in the reboiler and solid hexamethylcyclotrisiloxane again deposits in the condenser. Thus, hydrocarbon co-solvent (B) may be selected from aromatic compounds, such as o-xylene, m-xylene, p-xylene and ethyl benzene and aliphatic hydrocarbons, such as n-octane, n-nonane, methyloctane and cyclooctane, inter alia. It is also contemplated herein that mixtures of two or more of these co-solvents may be used as long as the resulting normal boiling point remains within the above described range. From a cost perspective, co-solvent (B) is preferably a technical grade mixture of xylene isomers.

As mentioned above, the mixture of hexamethylcyclotrisiloxane and co-solvent (B) obtained from the batch or continuous distillations according to the above described method can be used directly to prepare macromonomers having a narrow molecular weight distribution by reacting it in the presence of an alkyl lithium initiator, as taught in U.S. Pat. No. 5,399,649 to Okawa, hereby incorporated by reference.

EXAMPLES

The following examples are presented to further illustrate the method of this invention, but are not to be construed as limiting the invention, which is delineated in the appended claims. All parts and percentages in the examples are on a weight basis unless indicated to the contrary.

In the following examples GC analyses were performed on an HP 5890 A gas chromatograph (temperatures: oven=50° C., injector=150° C., detector=300° C., initial time=5 minutes, temperature rate 15° C./minute; gas flow rates variable). The percentage of $D_3$ in heptane or xylene was determined by preparing 50% solutions of hexamethylcyclotrisiloxane ($D_3$) in heptane or xylene and calibrating the GC peak area. The response factor of octamethylcyclotetrasiloxane ($D_4$) was considered to be similar to that of $D_3$. Gel permeation chromatography (GPC) analyses were run on a Waters 150 C. chromatograph (flow rate=1.2 ml/minute, injection volume=200 μL) in toluene against Polystyrene standards.

Example 1

A 3-liter three neck flask was equipped with a magnetic stirring bar, rubber septum (for sampling), an 18 inch (457 mm) glass distillation column and an azeotropic distillation head fitted with a finger condenser. The column was filled with glass helices (¼ inch ID from Scientific Glass Apparatus, Bloomfield, N.J.). The flask was charged with 1480 g of an acidic crude blend having the following approximate composition: heptane isomers=85%; $D_3$=10.5%; $D_4$=3.5%; —SiOH=trace amount.

To the flask there was added 300 g of reagent grade o-xylene. Distillation of the resulting solution was carried out at a pressure of 105–107 Torr. The following fractions were then collected:

Fraction No. 1 (up to 72° C.)=1267 g; GC composition: $D_3$=24.1 g (1.9%); remainder=heptane.

Fraction No. 2 (72° C.–84° C.)=275 g; (GC composition: $D_3$=131 g (47%); $D_4$=5.84 g (2.12%); xylene=138 g (50%). Residue in flask=229 g; (GC composition: $D_3$=31.8 g (14%); $D_4$=87 g (38.3%); xylene=110 g (48%).

No deposition of solid $D_3$ was observed in the column or on the finger condenser during the distillation.

The $D_3$/xylene solution (i.e., Fraction No. 2) was used to prepare a macromonomer having one SiOH terminal group by reacting in the presence of a butyl lithium initiator according to the methods described in the above cited patent to Okawa. The macromonomer had a number average molecular weight ($M_n$; obtained by GPC) of 10,310 and a polydispersity PD) of 1.07.

Example 2

The distillation procedure of Example 1 was repeated using 1004 g of the crude blend and 125 g of a technical grade xylene mixture. The distillation was carried out at a pressure of 105–107 Torr and the following fractions were collected:

Fraction No. 1 (up to 74° C.)=845 g (GC composition: $D_3$=15.64 g (1.8%); $D_4$=trace amount; remainder=heptane.

Fraction No. 2 (74° C.–82° C.)=183.2 g (GC composition: $D_3$=102.3 g 55.8%); $D_4$=3.26 g (1.78%); xylene=77.1 g (42.1%).

Residue in flask=87.4 g (GC composition: $D_3$=14.4 g (16.5%); $D_4$=53.4 g (61.4%); xytene=19 g (21.8%).

No deposition of solid $D_3$ was observed in the column or on the finger condenser during the distillation.

The above $D_3$/xylene solution (i.e., Fraction No. 2) was used to prepare a macromonomer having one SiOH terminal group by reacting in the presence of a butyl lithium initiator. The macromonomer $M_n$ was 8,430 and it had a PD of 1.07.

(Comparative) Example 3

The distillation procedure of Example 1 was repeated using 492 g of the crude blend. In this case, the co-solvent used was 101 g of technical grade toluene. Distillation was carried out at a pressure of 105–107 Torr and the following fractions were collected:

Fraction No. 1 (up to 41° C.)=356.3 g (GC composition: toluene=33.03 g (9.27%); $D_3$=0.18 g (0.05%).

Fraction No. 2 (41° C.–55° C.)=86.2 g (GC composition: toluene=47.5 g (55.09%); $D_3$=1.63 g (1.90%).

Fraction No. 3 (55° C.–67° C.)=25.1 g (GC composition: toluene=22 g (87.87%); $D_3$=2.74 g (10.92%).

In this example, the GC values reported are uncorrected area percents. After Fraction No. 3 was obtained the distillation had to be terminated since the top of the column was clogged by solid $D_3$. An attempt to continue the distillation by heating the column with a hot air blower but, after several minutes, the column was again plugged. At this point, there were 95 g of residue in the flask.

That which is claimed is:

1. A method for distilling a crude blend of hexamethylcyclotrisiloxane and higher cyclopolysiloxanes, said method comprising (I) mixing said crude blend with a hydrocarbon co-solvent having a normal boiling point of 125° C. to 150° C.; and (II) distilling the mixture formed in step (I) in an apparatus comprising a reboiler, a fractionating column and a condenser, wherein a solution of said hexamethylcyclotrisiloxane in said co-solvent is separated from said higher cyclopolysiloxans and deposition of solid hexamethylcyclotrisiloxane in said condenser is essentially prevented.

2. The method according to claim 1, wherein the normal boiling point of said co-solvent is 130° C. to 140° C.

3. The method according to claim 1, wherein said co-solvent is selected from the group consisting of o-xylene, m-xylene, p-xylene, ethyl benzene, cyclooctane, n-octane, n-nonane and methyloctane.

4. The method according to claim 1, wherein said co-solvent is a mixture of xylene isomers.

5. The method according to claim 1, wherein said mixing and said distilling steps are carried out in a continuous fashion.

6. The method according to claim 5, wherein the normal boiling point of said co-solvent is 130° C. to 140° C.

7. The method according to claim 5, wherein said co-solvent is selected from the group consisting of o-xylene, m-xylene, p-xylene, ethyl benzene, cyclooctane, n-octane, n-nonane and methyloctane.

8. The method according to claim 5, wherein said co-solvent is a mixture of xylene isomers.

9. The method according to claim 1, wherein said crude blend is obtained from a hydrolysis of dimethyldichlorosilane.

10. The method according to claim 9, wherein the normal boiling point of said co-solvent is 130° C. to 140° C.

11. The method according to claim 9, wherein said co-solvent is selected from the group consisting of o-xylene, m-xylene, p-xylene, ethyl benzene, cyclooctane, n-octane, n-nonane and methyloctane.

12. The method according to claim 9, wherein said co-solvent is a mixture of xylene isomers.

13. The method according to claim 1, wherein said crude blend is obtained from a base equilibration of at least one polydimethylsiloxane.

14. The method according to claim 13, wherein the normal boiling point of said co-solvent is 130° C. to 140° C.

15. The method according to claim 13, wherein said co-solvent is selected from the group consisting of o-xylene, m-xylene, p-xylene, ethyl benzene, cyclooctane, n-octane, n-nonane and methyloctane.

16. The method according to claim 13, wherein said co-solvent is a mixture of xylene isomers.

17. A method for distiling a crude blend of hexamethylcyclotrlsiloxane and higher cyclopolysiloxanes, said method comprising (I) mixing said crude blend with a hydrocarbon co-solvent having a normal boiling point of 125° C. to 150° C.; and (II) distilling the mixture formed in step (I) at atmospheric pressure in an apparatus comprising a reboiler, a fractionating column and a condenser, the amount of said co-solvent being adjusted such that the concentration of hexamehylyclotrisiloxane in the condenser is 30 to 50 weight percent, wherein a solution of said hexamethylyclotrisiloxane in said co-solvent is separated from said higher cyclopolysiloxanes and deposition of solid hexamethylcyclotrisiloxane in said condenser is essentially prevented.

18. The method according to claim 17, wherein said co-solvent is selected from the group consisting of o-xylene, m-xylene, p-xylene, ethyl benzene, cyclooctane, n-octane, n-nonane and methyloctane.

19. The method according to claim 18, wherein said co-solvent is a mixture of xylene isomers.

20. The method according to claim 17, wherein said mixing and said distilling steps are carried out in a continuous fashion.

21. The method according to claim 20, wherein said co-solvent is selected from the group consisting of o-xylene, m-xylene, p-xylene, ethyl benzene, cyclooctane, n-octane, n-nonane and methyloctane.

22. The method according to claim 21, wherein said co-solvent is a mixture of xylene isomers.

* * * * *